(12) United States Patent
Cai et al.

(10) Patent No.: US 12,252,716 B2
(45) Date of Patent: Mar. 18, 2025

(54) STRAIN AND METHOD FOR PRODUCING ROSMARINIC ACID

(71) Applicant: Hong-Taoism Research Institute of analytical science and technology LTD., Shaanxi Province, Xi'an (CN)

(72) Inventors: Yujie Cai, Wuxi (CN); Yi Yan, Xi'an (CN); Yanrui Ding, Wuxi (CN); Yajun Bai, Xi'an (CN); Xiaohui Zheng, Xi'an (CN)

(73) Assignee: Hong-Taoism Research Institute of analytical science and technology LTD., Shaanxi Province, Xi'an (CN)

( * ) Notice: Subject to any disclaimer, the term of this patent is extended or adjusted under 35 U.S.C. 154(b) by 1031 days.

(21) Appl. No.: 17/209,449

(22) Filed: Mar. 23, 2021

(65) Prior Publication Data

US 2021/0207105 A1    Jul. 8, 2021

Related U.S. Application Data

(63) Continuation of application No. PCT/CN2020/076363, filed on Feb. 24, 2020.

(30) Foreign Application Priority Data

Jun. 25, 2019 (CN) .......................... 201910554108.8

(51) Int. Cl.
| | | |
|---|---|---|
| *C12N 9/10* | (2006.01) | |
| *C12N 1/21* | (2006.01) | |
| *C12N 9/00* | (2006.01) | |
| *C12N 9/12* | (2006.01) | |
| *C12P 7/62* | (2022.01) | |

(52) U.S. Cl.
CPC ......... *C12N 9/1029* (2013.01); *C12N 9/1229* (2013.01); *C12N 9/93* (2013.01); *C12P 7/62* (2013.01); *C12Y 203/0114* (2013.01); *C12Y 207/04001* (2013.01); *C12Y 602/01012* (2013.01)

(58) Field of Classification Search
None
See application file for complete search history.

(56) References Cited

U.S. PATENT DOCUMENTS

| 5,011,775 | A | * | 4/1991 | Rao | ............................ | C12P 7/62 |
| | | | | | | 435/190 |
| 2004/0202731 | A1 | * | 10/2004 | Gow | ........................ | A61P 9/04 |
| | | | | | | 514/33 |
| 2006/0172402 | A1 | | 8/2006 | Havkin-Krenkel et al. | | |
| 2013/0315983 | A1 | | 11/2013 | Einbond et al. | | |

FOREIGN PATENT DOCUMENTS

| CN | 102061301 A | 5/2011 |
| CN | 102876713 A | 1/2013 |
| CN | 103834685 A | 6/2014 |
| CN | 109880862 A | 6/2019 |

OTHER PUBLICATIONS

Jiang et al., Engineered synthesis of rosmarinic acid in *Escherichia coli* resulting production of a new intermediate, caffeoylphenyl-lactate, Biotechnol. Lett. 28, 2016, 81-88. (Year: 2016).*
Lin et al., Whole-cell biocatalysts by design, Microb. Cell. Fact. 16, 2017, 106. (Year: 2017).*
Suzuki et al., Production of aminoacyl prolines using the adenylation domain of nonribosomal peptide synthetase with class III polyphosphate kinase 2-mediated ATP regeneration, J. Biosci. Bioeng. 125, 2018, 644-48. (Year: 2018).*
Kameda et al., A novel ATP regeneration system using polyphosphate-AMP phosphotransferase and polyphosphate kinase, J. Biosci. Bioeng. 91, 2001, 557-63. (Year: 2001).*
Iwamoto et al., Use of an *Escherichia coli* Recombinant Producing Thermostable Polyphosphate Kinase as an ATP Regenerator to Produce Fructose 1,6-Diphosphate, Appl. Environ. Microbiol. 73, 2007, 5676-78. (Year: 2007).*
Yan et al., Production of rosmarinic acid with ATP and CoA double regenerating system, Enz. Microb. Technol. 131, 2019, 109392. (Year: 2019).*
Liu et al., De novo biosynthesis of resveratrol by site-specific integration of heterologous genes in *Escherichia coli*, FEMS Microbiol. Lett. 363, 2016, fnw061. (Year: 2016).*
Bloch et al., Construction of a Chimeric Biosynthetic Pathway for the De Novo Biosynthesis of Rosmarinic Acid in *Escherichia coli*, ChemBioChem 15, 2014, 2393-2401. (Year: 2014).*
Yan Yi et al "Production of rosmarinic acid with ATP and CoA double regenerating" Engzyme and Microbial Technology, May 8, 2019, V131 ISSA 1879-0909 p. 1-6.
Jiang jingjie et al. "engineered synthesis of a new intermediate, caffeoyl-phenyllactate" Biotechnology Letters Sep. 4, 2015, V1 Issue 38 p. 81-88.
Zhuang yibin et al "synthesis of rosmarinic acid analogues in *Escherichia coli*" Biotech Letters Dec. 14, 2015 V4 Issue 28, p. 619-627.
Bloch SE et al. "Construction of a chimeric biosynthetic pathway for the de novo biosynthesis of rosmarinic acid in *Escherichia coli*" Biotech Letters Sep. 9, 2014, V16 Issue 15 p. 2393-2401.

* cited by examiner

*Primary Examiner* — Todd M Epstein
(74) *Attorney, Agent, or Firm* — IPRO, PLLC

(57) ABSTRACT

The disclosure discloses a strain and method for producing rosmarinic acid, and belongs to the technical field of bioengineering. The disclosure constructs a recombinant cell or a combination of recombinant cells expressing 4-coumarate:CoA ligase, rosmarinic acid synthase, polyphosphate kinase 2-I (PPK2-I) and polyphosphate kinase 2-II (PPK2-II), and utilizes the recombinant cell or the combination of recombinant cells to catalyze Danshensu and caffeic acid for synthesizing rosmarinic acid. The disclosure has good industrial application prospects.

13 Claims, 1 Drawing Sheet

STRAIN AND METHOD FOR PRODUCING ROSMARINIC ACID

TECHNICAL FIELD

The disclosure relates to a strain and method for producing rosmarinic acid, and belongs to the technical field of bioengineering.

BACKGROUND

Rosmarinic acid (RA) is a natural polyphenol compound. RA is an ester composed of caffeic acid and D-Danshensu, and is widely distributed in plants such as Lamiaceae, Boraginaceae, Cucurbitaceae, Tiliaceae, and Umbelliferae. Compared with other plants, Lamiaceae and Boraginaceae have the highest content of RA. As the most effective antioxidant component in rosemary, RA has been recognized by the US Food and Drug Administration (FDA) as a "public safety food". As early as 1998, Nakamura et al. proposed that the o-diphenol hydroxyl group is the structural basis for scavenging the free radical activity, and the conjugated double bond at the C3 position has a synergistic effect (Ohto Y, Murakami A, Nakamura Y, et al. Superoxide scavenging activity of rosmarinic acid from *Perilla frutescens* Britton var. *acuta* f. *viridis* [J]. Journal of Agricultural and Food Chemistry, 1998, 46(11): 4545-4550). Studies in recent years have shown that rosmarinic acid has obvious effects on many diseases. Rosmarinic acid has good biological activity in anti-oxidation, pathogenic microorganism inhibition, anti-cancer and anti-tumor, anti-inflammatory and immunosuppressive activities, anti-thrombosis, anti-platelet aggregation, anti-depression, radiation protection, cell damage and memory damage prevention, etc. As people continue to study the biological activity of rosmarinic acid and the metabolic characteristics thereof in the body, more and more biological activities of RA have been developed. Therefore, further reasonable development and utilization of rosmarinic acid for human use will become a research hotspot.

At present, the industrial production method of rosmarinic acid is not yet mature, and most of them are in the laboratory stage. There are two main methods for preparing a small amount of rosmarinic acid: 1) preparation of rosmarinic acid by performing cellulase enzymatic hydrolysis, ultrasonication, and reflux treatment on plants of the Lamiaceae family, and then performing extraction; and 2) preparation of rosmarinic acid by chemical synthesis. The 1) method for extracting rosmarinic acid from plants is simple and easy to implement, and the product quality is guaranteed. However, the method requires the use of a large amount of organic solvents, the extraction process takes a long time and the recovery rate of rosmarinic acid is not high. Although the 2) method of chemical synthesis of rosmarinic acid can successfully synthesize rosmarinic acid, due to the high cost of raw materials and reagents, many by-products, long synthesis steps, and fierce reactions that are difficult to control, the method is not suitable for industrial production. In addition, because rosmarinic acid is an important raw material for foods, medicines, and health products, products obtained through chemical methods are not welcome. At present, the rosmarinic acid on the market is mainly extracted from plants. For example, Chinese invention patent CN 108658769 A discloses an extraction process of Prunella vulgaris rosmarinic acid based on a response surface method; Chinese invention patent CN 107935855 A discloses a method for extracting rosmarinic acid from rosemary by a reflux method. However, due to limited plant resources, limited rosmarinic acid in plants, and cumbersome and complicated extraction processes, rosmarinic acid extracted from plants is expensive. Therefore, production by microbiological methods has received extensive attention.

In 2014, Bloch et al. proposed to use tyrosine and 4-hydroxyphenylpyruvic acid produced by the metabolism of *Escherichia coli* as substrates, and under the action of hydroxy acid dehydrogenase, the endogenous 4-hydroxyphenylpyruvic acid is transformed into 4-hydroxyphenyllactic acid; then, the hydroxylase HpaBC cloned from *Escherichia coli* is used for performing meta-hydroxylation to obtain 3,4-dihydroxyphenyllactic acid; at the same time, endogenous tyrosine is used as a substrate to generate caffeic acid; first, tyrosine is used to produce p-coumaric acid under the action of tyrosine ammonia lyase; then, the hydroxylase HpaBC cloned from *Escherichia coli* is used to perform meta-hydroxylation to obtain caffeic acid; after the caffeic acid is obtained, caffeyl-CoA is generated under the action of 4-coumaric acid-CoA ligase; and finally, the caffeyl-CoA and 3,4-dihydroxyphenyllactic acid are transformed to 1.8±0.3 μm rosmarinic acid after 72 hours under the action of rosmarinic acid synthase (Construction of a chimeric biosynthetic pathway for the de novo biosynthesis of rosmarinic acid in *Escherichia coli*. Chembiochem, 15(16): 2393-2401 (2014)). However, the HpaBC enzyme activity is low in the method, resulting in an extremely low yield of rosmarinic acid. Some people have also tried to use *Escherichia coli* overexpressing the 4-coumarate: CoA ligase and the rosmarinic acid synthase to convert caffeic acid and Danshensu to produce rosmarinic acid. However, due to the lack of coenzyme and a rapid regeneration system, the yield is extremely low (Synthesis of rosmarinic acid analogues in *Escherichia coli*, Biotechnol Lett38: 619-627 (2016)).

SUMMARY

The disclosure discloses a method for synthesizing rosmarinic acid using phenolic acids as substrates to increase the yield of synthetic rosmarinic acid by a biological method or enzymatic method. At the same time, the method disclosed by the disclosure can synthesize L-rosmarinic acid.

The disclosure provides a method for synthesizing rosmarinic acid using phenolic acids as substrates, wherein the phenolic acids include caffeic acid and Danshensu; the caffeic acid is linked to coenzyme A (CoA) by 4-coumarate: CoA ligase to produce caffeyl-CoA; and rosmarinic acid synthase uses the energy of ATP to synthesize the caffeyl-CoA and Danshensu into rosmarinic acid. In the process, CoA is released and ATP is hydrolyzed into AMP. Polyphosphate kinase 2-II (PPK2-II) produces ADP from AMP, and further ATP is regenerated from ADP by polyphosphate kinase 2-I (PPK2-I).

In one example, the 4-coumarate: CoA ligase is derived from Scutellaria *baicalensis, Ocimum tenuiflorum, Ocimum basilicum, Arabidopsis thaliana, Penicillium chrysogenum, Streptomyces coelicolor* A3 (2), or *Rhodococcus jostii* RHA1. Alternatively, the amino acid sequence of the 4-coumarate: CoA ligase is the sequence with the accession NO. BAD90936.1, ADO16242.1, AGP02119.1, AAD47193.1, CAA04820.1, CAB95894.1, or ABG96911.1 on NCBI. Alternatively, the nucleotide sequence of the 4-coumarate: CoA ligase is the sequence with the accession NO. AB166767.1 REGION: 42 . . . 1691, HM990148.1 REGION: 1 . . . 1704, KC576841.1 REGION: 1 . . . 1704, AF106086.1 REGION: 67 . . . 1737, AJ001540.1 REGION:

89 . . . 1825, AL645882 REGION: complement (4799-896 . . . 4801464), or CP000431.1 REGION: complement (5466961 . . . 5468496) on NCBI.

In one example, the PPK2-I is from *Sinorhizobium_meliloti*. Alternatively, the amino acid sequence of PPK2-I is the sequence with the accession NO. NP_384613.1 on NCBI. Alternatively, the nucleotide sequence of PPK2-I is the sequence with the accession NO. NC_003047 REGION: complement (564142 . . . 565044) on NCBI.

In one example, the rosmarinic acid synthase is from *Plectranthus scutellarioides*, *Lavandula angustifolia*, *Melissa officinalis*, *Salvia miltiorrhiza*, *Coffea canephora*, *Nicotiana tabacum*, or *Dianthus caryophyllus*. Alternatively, the amino acid sequence of the rosmarinic acid synthase is the sequence with the accession NO. CAK55166.1, ABI48360.1, CBW35684.1, ADA60182.1, ABO47805.1, CAE46932.1, or CAB06430.1 on NCBI. Alternatively, the nucleotide sequence of the rosmarinic acid synthase is the sequence with the accession NO. AM283092.1, DQ886904.1 REGION: 51 . . . 1433, FR670523.1, FJ906696.1, EF137954.1 REGION: 3 . . . 1307, AJ582651.1, or Z84386.1 REGION: 137 . . . 1477 on NCBI.

In one example, the PPK2-II is from *Acinetobacter johnsonii*. Alternatively, the amino acid sequence of the PPK2-II is the sequence with the accession NO. BAC76403.1 on NCBI. Alternatively, the nucleotide sequence of the PPK2-II is the sequence with the accession NO. AB092983 REGION: 339 . . . 1766 on NCBI.

In one example, the Danshensu is D-Danshensu or L-Danshensu. When the Danshensu is L-Danshensu, the rosmarinic acid synthase is from *Coffea canephora* or *Dianthus caryophyllus*.

The disclosure also provides a recombinant cell capable of synthesizing rosmarinic acid using phenolic acids as substrates or a combination of recombinant cells capable of synthesizing rosmarinic acid using phenolic acids as substrates. The recombinant cell expresses 4-coumarate: CoA ligase, rosmarinic acid synthase, polyphosphate kinase 2-II (PPK2-II), and polyphosphate kinase 2-1 (PPK2-1). The combination of recombinant cells includes recombinant cells expressing one or more of 4-coumarate: CoA ligase, rosmarinic acid synthase, PPK2-II, and PPK2-I respectively, and each recombinant cell does not repeatedly express one of 4-coumarate: CoA ligase, rosmarinic acid synthase, PPK2-II, and PPK2-I expressed by other recombinant cells.

*Escherichia coli* can be selected as a host for both the recombinant cell or the combination of recombinant cells, for example *Escherichia coli* BL21 (DE3).

The four enzymes can be expressed in the host by means of vectors for expression, fusion expression or co-expression, or integrated into the genome of the host for expression. When the four enzymes are expressed by means of vectors, one or more vectors can be selected to express one or more of the four enzymes.

For the recombinant cell, 4-coumarate: CoA ligase, rosmarinic acid synthase, PPK2-I, and PPK2-II are co-expressed in a host by means of vectors or integrated into the genome of the host for expression; and when 4-coumarate: CoA ligase, rosmarinic acid synthase, PPK2-I, and PPK2-II are expressed by means of vectors, a plurality of vectors are selected, and each vector expresses one or more of the four enzymes, or one vector is selected to express the four enzymes simultaneously. For example, genes encoding 4-coumarate: CoA ligase, rosmarinic acid synthase, PPK2-I, and PPK2-II are assorted onto one or more of four plasmids pETDuet-1, pACYCDuet-1, pRSFDuet-1, and pCDFduet-1, and each of the plasmids carries one or more of the genes encoding 4-coumarate: CoA ligase, rosmarinic acid synthase, PPK2-I, and PPK2-II. For another example, *Escherichia coli* is used as a host to express genes encoding rosmarinic acid synthase derived from *Cofea canephora* or *Dianthus caryophyllus*, and genes encoding PPK2-I, PPK2-II, and 4-coumarate: CoA ligase; pRSFDuet-1 is used as a vector to express genes encoding PPK2-I and PPK2-II, and pTDuet-1 is used as a vector to express genes encoding 4-coumarate: CoA ligase and rosmarinic acid synthase; and the genes encoding 4-coumarate: CoA ligase, rosmarinic acid synthase, PPK2-1, and PPK2-II all include T7 promoters and RBS binding sites before the genes, and T7 terminators behind the genes.

For the combination of the recombinant cells, 4-coumarate: CoA ligase, rosmarinic acid synthase, PPK2-I, and PPK2-II are co-expressed in the host by means of vectors or integrated into the genome of the host for expression. For example, genes encoding 4-coumarate: CoA ligase, rosmarinic acid synthase, PPK2-I, and PPK2-II are assorted onto one or more of four plasmids pETDuet-1, pACYCDuet-1, pRSFDuet-1, and pCDFduet-1, and each plasmid carries one or more of the genes encoding 4-coumarate: CoA ligase, rosmarinic acid synthase, PPK2-I, and PPK2-II. For another example, *Escherichia coli* is used as a host, pRSFDuet-1 is used as a vector to express genes encoding PPK2-I and PPK2-II, and pTDuet-1 is used as a vector to express genes encoding 4-coumarate: CoA ligase and rosmarinic acid synthase; and the genes encoding the 4-coumarate: CoA ligase, rosmarinic acid synthase, PPK2-I, and PPK2-II all include T7 promoters and RBS binding sites before the genes, and T7 terminators behind the genes.

In particular, the disclosure also provides a recombinant cell capable of synthesizing L-rosmarinic acid using caffeic acid and L-Danshensu as substrates, and the recombinant cell expresses genes encoding rosmarinic acid synthase derived from *Coffea canephora* or *Dianthus caryophyllus*, and genes encoding PPK2-1, PPK2-II, and 4-coumarate: CoA ligase. The recombinant cell uses *Escherichia coli* as a host, uses pRSFDuet-1 as a vector to express genes encoding PPK2-I and PPK2-II, and uses pTDuet-1 as a vector to express genes encoding 4-coumarate: CoA ligase and rosmarinic acid synthase. Each gene includes a T7 promoter and an RBS binding site before the gene, and a T7 terminator behind the gene.

The disclosure also provides a method for whole-cell catalytic production of rosmarinic acid, including the steps: (1) preparing the recombinant cell or the combination of recombinant cells, and (2) synthesizing D-rosmarinic acid (L-rosmarinic acid) using the recombinant cell or the combination of recombinant cells prepared in step (1) as a catalyst, and using caffeic acid and D-Danshensu (L-Danshensu) as substrates. The preparation in step (1) includes culturing and propagating recombinant cells or a combination of recombinant cells, allowing the recombinant cells or the combination of recombinant cells to express four enzymes, and then collecting the recombinant cells. When the whole-cell catalyst is used, in addition to substrates, an appropriate temperature and pH are also necessarily maintained, and if necessary, some coenzymes or nutrients are also provided to help the whole-cell catalyst perform a better catalytic effect.

In one example, the whole-cell transformation production system includes 1-200 g/L (wet weight) cells, 1-100 g/L Danshensu (D or L), 1-100 g/L caffeic acid, 0-1 g/L ATP, 0-1 g/L CoA, and 300 g/L sodium hexametaphosphate, and has a pH of 5.0-9.0; the reaction temperature is 15-40° C., and the reaction time is 1-48 hours.

In one example, the recombinant cells are reacted in a reaction system containing D-Danshensu, caffeic acid, CoA, ATP and sodium hexametaphosphate at 15-30° C. for 5-48 hours.

In one example, the recombinant cells are reacted in a reaction system containing D-Danshensu, caffeic acid, CoA, ATP and sodium hexametaphosphate at 40° C. for 48 hours.

The disclosure constructs a genetically engineered strain strengthening expression of four kinds of enzymes to be applied to the production of rosmarinic acid. The substrates used in the disclosure are caffeic acid and Danshensu, and the two phenolic acids, namely caffeic acid and Danshensu, are easily available.

The disclosure uses a reasonable expression strategy to express 4-coumarate: CoA ligase and rosmarinic acid synthase, while also expressing PPK2-II and PPK2-I, thereby realizing dual coenzyme regeneration of ATP and CoA, effectively ensuring continuous progress of the enzyme-catalyzed reaction and increasing the yield of rosmarinic acid.

The Danshensu group of rosmarinic acid in nature is D-type, so common rosmarinic acid is D-type. The disclosure obtains rosmarinic acid synthase capable of using L-Danshensu as a substrate. On the basis, L-danshensu and caffeic acid are used as raw materials to obtain L-rosmarinic acid through biological synthesis.

DETAILED DESCRIPTION

Figure 1:
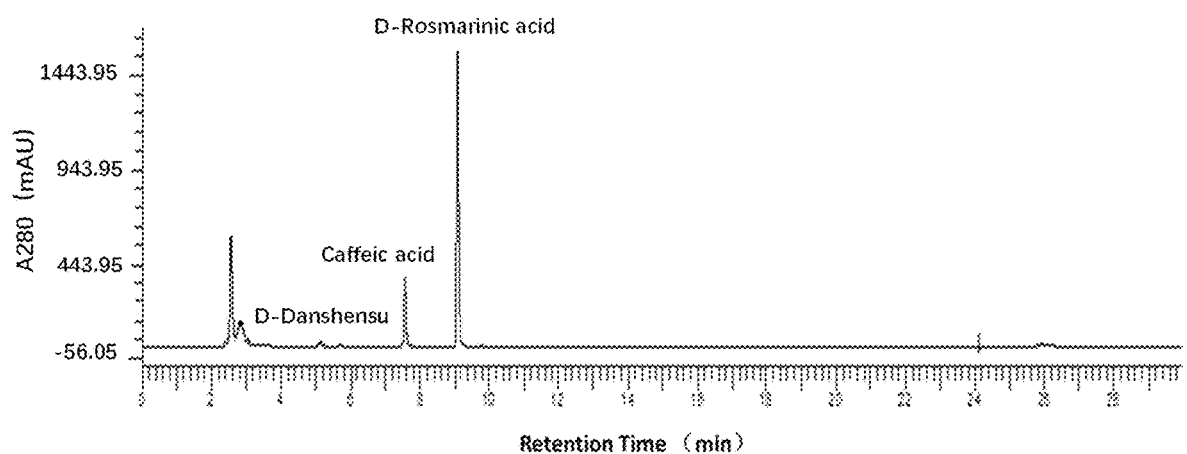
FIG. 1 is the liquid chromatogram of rosmarinic acid synthesized in Example 4.

1. Strains and Plasmids Involved in the Following Examples
   pRSFDuet-1, pETDuet-1, pCDFDuet-1 and pACYC-Duet-1 plasmids, and *Escherichia coli* BL21 (DE3) were all purchased from Novagen.
2. Construction of Multi-Gene Co-Expression System and Cell Culture At present, there are many methods for co-expression of multiple genes in *Escherichia coli* (for example, the method described in the article "Multi-gene co-expression strategy in *Escherichia coli*, China Biotechnology, 2012, 32(4): 117-122"). The disclosure uses the method described in Liu Xianglei's doctoral dissertation (Production of Shikimic Acid and Resveratrol by Transformation of *Escherichia coli* by Synthetic Biology Technology, 2016, Shanghai Institute of Pharmaceutical Industry) to construct recombinant *Escherichia coli*. In the following examples, when multiple genes are co-expressed, each gene includes a T7 promoter and an RBS binding site before the gene, and a T7 terminator behind the gene. Theoretically, because each gene has T7 and RBS in front, the expression intensity of the gene is not affected by the order of the gene on a plasmid. The constructed plasmid is thermally transduced into *Escherichia coli* competent cells, and spread on a monoclonal antibody or mixed antibiotic solid plate, and positive transformants are screened to obtain recombinant *Escherichia coli*.

Culture of cells: According to a classical recombinant *Escherichia coli* culture and induction expression scheme, recombinant *Escherichia coli* is transferred to an LB fermentation medium (10 g/L peptone, 5 g/L yeast powder, and 10 g/L NaCl) at a volume percentage of 2%. After the cell $OD_{600}$ reaches 0.6-0.8, IPTG with a final concentration of 0.4 mM is added, and expression culture is induced at 20° C. for 8 h. After expression induction is completed, the cells are collected by centrifugation at 4° C. and 8000 rpm for 20 minutes.

3. Selection of Related Enzymes
(1) Polyphosphate Kinase 2-I (PPK2-I)
The gene smpkk encoding PPK2-I derived from *Sinorhizobium_meliloti* was selected. The accession NO. of the gene smpkk on NCBI is NC_003047 REGION: complement (564142 . . . 565044), and the corresponding amino acid sequence is NP_384613.1.
(2) Polyphosphate Kinase 2-II (PPK2-II)
The gene ajpkk encoding PPK2-II derived from *Acinetobacter johnsonii* was selected. The accession NO. of the sequence of the gene ajpkk on NCBI is AB092983 REGION: 339 . . . 1766, and the corresponding amino acid sequence is BAC76403.1.
(3) 4-Coumarate: CoA Ligase
Refer to example 1.
(4) Rosmarinic Acid Synthase
Refer to example 2.

4. Detection and Analysis of Samples

Reference for the measuring method of rosmarinic acid content: Enhanced accumulation of caffeic acid, rosmarinic acid and luteolin-glucoside in red *Perilla* cultivated under red diode laser and blue LED illumination followed by UV-A irradiation. Journal of functional foods 2 (2010) 66-70. The solubility of Danshensu, caffeic acid, and rosmarinic acid is relatively low. In the transformation process of the disclosure, an excessive amount of substrate is added, the substrate will dissolve while reacting, and the product will precipitate while reacting under high concentration conditions. When measuring, pure water is added to make the product completely dissolved before measuring.

Reference for measuring the activity of rosmarinic acid synthase: Rosmarinic acid synthase is a new member of the superfamily of BAHD acyltransferases, Planta, 2006, 224: 1503-1510.

Reference for measuring the activity of 4-coumarate: CoA ligase: 4-Coumarate: CoA ligase from cell suspension cultures of *Petroselinum hortense* Hoffm. Arch. Biochem. Biophys. 1977, 184, 237-248.

Specific enzyme activity (U $mg^{-1}$) is defined as the unit of enzyme activity per mg enzyme. An enzyme activity unit (U) is defined as the amount of enzyme required to produce 1 μmol of product in 1 min.

Example 1: Screening and Expression of 4-Coumarate: CoA Ligase 4-coumarate: CoA ligase is widely present in various organisms. According to the gene information of the 4-coumarate: CoA ligase in Scutellaria *baicalensis, Ocimum tenuiflorum, Ocimum basilicum, Arabidopsis thaliana, Penicillium chrysogenum, Streptomyces coelicolor* A3 (2), and *Rhodococcus jostiid* on NCBI, 4-coumarate: CoA genes sb4cl, ot4cl, ob4cl, at4cl, pc4cl, sc4cl, and rj4cl were obtained by complete synthesis. The accession NOs. of the amino acid sequences corresponding to the genes on NCBI are: BAD90936.1, ADO16242.1, AGP02119.1, AAD47193.1, CAA04820.1, CAB95894.1, and ABG96911.1. The synthesized genes were ligated to the pETDuet-1 vector and induced for expression in *Escherichia coli* BL21 (DE3). The expression induction method is: recombinant *Escherichia coli* was transferred to an LB fermentation medium (containing 10 g/L peptone, 5 g/L yeast powder and 10 g/L NaCl) at a volume percentage of 2% for performing fermentation culture; and after the cell OD$_{600}$ reached 0.6-0.8, IPTG with a final concentration of 0.4 mM was added, and expression culture was induced at 20° C. for 8 h. After expression induction is completed, the fermentation broth was centrifuged at 4° C. and 8000 rpm for 20 minutes, and cells were collected. The collected cells were crushed, and a Histag tag was used to purify the cell crushing liquid to obtain the pure enzyme. After the pure enzyme was obtained, the activity of the pure enzyme was measured.

When caffeic acid and coenzyme A were used as substrates, the specific enzyme activity of the enzymes expressed by the 4-coumarate: CoA ligase genes sb4cl, ot4cl, ob4cl, at4cl, pc4cl, sc4cl, and rj4cl was respectively: 152, 143, 161, 179, 202, 174, and 88 U/mg.

Example 2: Screening and Expression of Rosmarinic Acid Synthase

Rosmarinic acid synthase mainly exists in plants. According to the gene information of the rosmarinic acid synthase in *Plectranthus scutellarioides, Lavandula angustifolia, Melissa officinalis, Salvia miltiorrhiza, Coffea canephora, Nicotiana tabacum*, and *Dianthus caryophyllus* on NCBI, rosmarinic acid synthase genes psras, laras, moras, smras, ccras, ntras, and dcras were obtained by complete synthesis. The accession NOs. of the amino acid sequences corresponding to the genes on NCBI are: CAK55166.1, ABI48360.1, CBW35684.1, ADA60182.1, ABO47805.1, CAE46932.1, and CAB06430.1. The synthesized genes were respectively ligated to pETDuet-1 vector, and expressed and purified in the same way as in Example 1.

When caffeyl-CoA and D-Danshensu were used as substrates, the specific enzyme activity of the enzymes expressed by rosmarinic acid synthase genes psras, laras, moras, smras, ccras, ntras, and dcras was respectively: 410, 320, 414, 233, 361, 521, and 371 U/mg.

When caffeyl-CoA and L-Danshensu were used as substrates, the specific enzyme activity of the enzymes expressed by rosmarinic acid synthase genes psras, laras, moras, smras, ccras, ntras, and dcras was respectively: 0, 0, 0, 0, 120, 0, and 142 U/mg. It can be seen that only the rosmarinic acid synthase encoded by ccras and dcras has the ability to synthesize rosmarinic acid with L-Danshensu as a substrate.

Example 3: Construction of Recombinant *Escherichia coli* Expressing Four Enzymes Simultaneously Construction of Recombinant *Escherichia coli*:

As shown in Table 1, selection was made from four plasmids pETDuet-1, pACYCDuet-1, pRSFDuet-1, and pCDFduet-1, and the genes encoding the four enzymes were ligated to the same plasmid, or ligated to two plasmids separately (2 genes expressed on each plasmid), or ligated to the four plasmids (1 gene expressed on each plasmid). Each gene included a T7 promoter and an RBS binding site before the gene, and a T7 terminator behind the gene. The constructed recombinant plasmids were transformed into *Escherichia coli* BL21, and positive transformants were obtained by screening with a mixed antibiotic plate to obtain recombinant *Escherichia coli* capable of strengthening expression of 4 genes.

The recombinant *Escherichia coli* was induced for expression, and bacterial cells were collected after the expression induction was completed. A 100 mL reaction system, containing 200 g/L (wet weight) cells, 20 g/L D-Danshensu, 20 g/L caffeic acid, 1 g/L CoA, 1 g/L ATP, and 60 g/L sodium hexametaphosphate, and having a pH of 8, was constructed. The 100 ml reaction system was placed at 30° C. for reaction for 24 hours. The solubility of the Danshensu and caffeic acid is very small, so in the reaction process, the Danshensu and caffeic acid were dissolved while being consumed. After the reaction, the reaction solution was diluted and the concentration of rosmarinic acid in the reaction solution was measured by liquid chromatography. The results are shown in Table 1.

TABLE 1

| Recombinant strains | Rosmarinic acid g/L |
| --- | --- |
| *Escherichia coli* BL21(DE3)/pRSFDuet-1-smpkk-ajpkk+pETDuet-1-pc4cl -ntras | 34 |
| *Escherichia coli* BL21(DE3)/pCDFDuet-1-smpkk-ajpkk+pACYCDuet-1-pc4cl-ntras | 32 |
| *Escherichia coli* BL21(DE3)/pRSFDuet-1-smpkk+pETDuet-1-ajpkk+pCDFDuet-1-pc4cl+pACYCDuet-1-ntras | 22 |
| *Escherichia coli* BL21(DE3)/pRSFDuet-1-smpkk-ajpkk-pc4cl-ntras | 26 |
| *Escherichia coli* BL21(DE3)/pETDuet-1-smpkk-ajpkk-pc4cl-ntras | 28 |
| *Escherichia coli* BL21(DE3)/pACYCDuet-1-smpkk-ajpkk-pc4cl-ntras | 14 |
| *Escherichia coli* BL21(DE3)/pRSFDuet-1-smpkk-ajpkk-pc4cl+pETDuet-1-ntras | 19 |
| *Escherichia coli* BL21(DE3)/pRSFDuet-1-smpkk-pc4cl+pETDuet-1-ntras-ajpkk | 33 |
| *Escherichia coli* BL21(DE3)/pRSFDuet-1-smpkk-ntras+pETDuet-1-pc4cl-ajpkk | 31 |
| *Escherichia coli* BL21(DE3)/pRSFDuet-1-smpkk-ajpkk+pETDuet-1-sb4cl-psras | 9 |
| *Escherichia coli* BL21(DE3)/pRSFDuet-1-smpkk-ajpkk+pETDuet-1-ot4cl-laras | 30 |
| *Escherichia coli* BL21(DE3)/pRSFDuet-1-smpkk-ajpkk+pETDuet-1-ob4cl -moras | 31 |
| *Escherichia coli* BL21(DE3)/pRSFDuet-1-smpkk-ajpkk+pETDuet-1-at4cl-smras | 33 |
| *Escherichia coli* BL21(DE3)/pRSFDuet-1-smpkk-ajpkk+pETDuet-1-pc4cl-ccras | 29 |
| *Escherichia coli* BL21(DE3)/pRSFDuet-1-smpkk-ajpkk+pETDuet-1-rj4cl-dcras | 28 |
| *Escherichia coli* BL21(DE3)/pRSFDuet-1-smpkk-ajpkk+pETDuet-1-sc4cl-ccras | 16 |

Example 4: Synthesis of Rosmarinic Acid In Vitro Using Four Enzymes

The 4 genes smpkk, ajpkk, pc4cl, and ntras were respectively ligated to pEDTDuet-1 vectors to obtain 4 recombinant vectors. The 4 recombinant vectors were transformed into *Escherichia coli* BL21 respectively to obtain recombinant *Escherichia coli* expressing 4 enzymes. 4 pure enzymes were obtained after expression and purification using the same method as in Example 1. Then 2 mg of each of these four pure enzymes was added to the 100 mL reaction system containing 20 g/L D-Danshensu, 20 g/L caffeic acid, 1 g/L CoA, 1 g/L ATP, and 60 g/L sodium hexametaphosphate, and having a pH of 8; and reaction was performed at 30° C. for 5 hours. Finally, the liquid chromatographic measurement result indicated that the concentration of rosmarinic acid in the reaction solution was 36 g/L, and the liquid chromatogram was as shown in FIG. 1 of the specification.

Example 5: Synthesis of Rosmarinic Acid Using the Combination of Recombinant Cells Expressing smpkk, ajpkk, pc4cl, and ntras Genes Respectively The 4 genes smpkk, ajpkk, pc4cl, and ntras were respectively ligated to pEDTDuet-1 vectors to obtain 4 recombinant vectors. The 4 recombinant vectors were transformed into *Escherichia coli* BL21 respectively to obtain recombinant *Escherichia coli* respectively expressing one of 4 enzymes. Recombinant *Escherichia coli* expression enzymes were induced using the same method as in Example 1. Then four kinds of 20 g/L recombinant cells were added in a 100 mL reaction system containing 20 g/L D-Danshensu, 20 g/L caffeic acid, 1 g/L CoA, 1 g/L ATP, and 60 g/L sodium hexametaphosphate, and having a pH of 8, and reaction was performed at 30° C. for 5 hours. Finally, the liquid chromatographic measurement result indicated that the concentration of rosmarinic acid in the reaction solution was 23 g/L.

Example 6: Synthesis of L-Rosmarinic Acid by Recombinant *Escherichia coli* Whole-Cell Catalysis The Danshensu group of rosmarinic acid in nature is D-type. In the present example, L-Danshensu and caffeic acid were used as raw materials to synthesize L-rosmarinic acid (the difference between L-rosmarinic acid and D-rosmarinic acid is that the Danshensu group of L-rosmarinic acid is L-type). Previously, L-rosmarinic acid has not been synthesized by biological methods.

The genes ccras and dcras encoding the rosmarinic acid synthase derived from *Coffea canephora* and *Dianthus caryophyllus* were selected, together with the genes encoding PPK2-I, PPK2-II, and 4-coumarate: CoA ligase, to construct a recombinant strain *Escherichia coli* BL21 (DE3)/pRSFDuet-1-smpkk-ajpkk+pTDuet-1-pc4cl-dcras. According to the method in Example 1, the recombinant strain was induced for expression, and then bacterial cells were collected.

Figure 2:
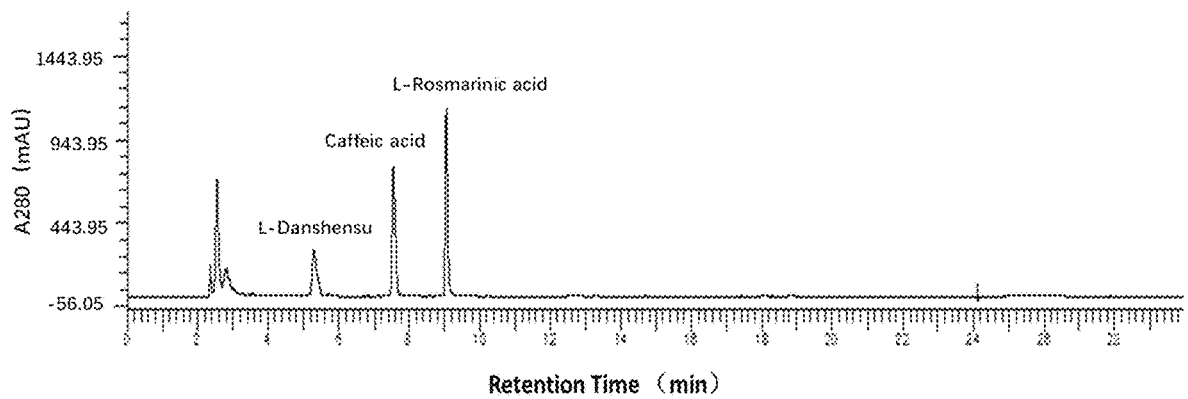
FIG. 2 is the liquid chromatogram of rosmarinic acid synthesized in Example 6.

In a 100 mL reaction system containing 100 g/L (wet weight) cells, 20 g/L L-Danshensu, 20 g/L caffeic acid, 1 g/L CoA, 1 g/L ATP, and 60 g/L sodium hexametaphosphate, and having a pH of 8, reaction was performed at 30° C. for 24 hours. After the transformation, the concentration of L-rosmarinic acid in the reaction solution was measured as 33 g/L by liquid chromatography, and the liquid chromatogram was as shown in FIG. 2 of the specification. The DAC-HB50 preparative chromatographic column of Jiangsu Hanbon Science & Technology Co., Ltd. was used to prepare purified samples. The preparative chromatographic conditions were: the mobile phase was 50% methanol, the column temperature was natural, the flow rate was 3 mL/min, and the injection volume was 5 mL. The chromatographic purity of the sample prepared for the first time reached 99.9%, and the product obtained after repeated injection and separation was spin-evaporated to dryness under vacuum at 50° C. 0.5 g of the sample evaporated to dryness was weighed and dissolved in deionized water and diluted to 50 mL, and the optical rotation was measured with the Japanese Atago AP-300 automatic polarimeter. The optical rotation is $[\alpha]_D^{20}=-15.5°$. Therefore, we can confirm that the rosmarinic acid prepared in the present example is L-rosmarinic acid.

Example 7: Synthesis of Rosmarinic Acid by Recombinant *Escherichia coli* Whole-Cell Catalysis The following 2 kinds of recombinant strains were constructed: *Escherichia coli* BL21 (DE3)/pRSFDuet-1-smpkk-ajpkk (named E1), and *Escherichia coli* BL21 (DE3)/pETDuet-1-sc4cl-ccras (named E2).

According to the method in Example 1, E1 and E2 were induced for expression respectively, and then bacterial cells were collected. In a 100 mL reaction system containing 30 g/L (wet weight) E1 cells, 50 g/L (wet weight) E2 cells, 100 g/L D-Danshensu, 10 g/L caffeic acid, 300 g/L sodium hexametaphosphate, 1 g/L CoA, and 1 g/L ATP, and having a pH of 9, reaction was performed at 40° C. for 48 hours. After the transformation, the content of rosmarinic acid was measured as 162 g/L by liquid chromatography.

Example 8: Synthesis of Rosmarinic Acid by Recombinant *Escherichia coli* Whole-Cell Catalysis The following 2 kinds of recombinant strains were constructed: *Escherichia coli* BL21 (DE3)/pRSFDuet-1-smpkk-ajpkk-at4cl (named E3), *Escherichia coli* BL21 (DE3)/pACYCDuet-1-ccras (named E4).

According to the method in Example 1, E3 and E4 were induced for expression respectively, and then bacterial cells were collected. In a 100 mL reaction system containing 100 g/L (wet weight) E3 cells, 100 g/L (wet weight) E4 cells, 1 g/L D-Danshensu, 1 g/L caffeic acid, 0.5 g/L CoA, 1 g/L ATP, and 3 g/L sodium hexametaphosphate, and having a pH of 5, reaction was performed at 15° C. for 48 hours. After the transformation, the content of rosmarinic acid was measured as 1.3 g/L by liquid chromatography.

Example 9: Synthesis of Rosmarinic Acid by Recombinant *Escherichia coli* Whole-Cell Catalysis The following 2 kinds of recombinant strains were constructed: *Escherichia coli* BL21 (DE3)/pRSFDuet-1-ntras-at4cl (named E5), and *Escherichia coli* BL21 (DE3)/pACYCDuet-1-smpkk-ajpkk (named E6).

According to the method in Example 1, E5 and E6 were induced for expression respectively, and then bacterial cells were collected. In a 100 mL reaction system containing 100 g/L (wet weight) E5 cells, 100 g/L (wet weight) E6 cells, 1 g/L D-Danshensu, 1 g/L caffeic acid, 3 g/L sodium hexametaphosphate 1 g/L CoA, and 0.5 g/L ATP, and having a pH of 7, reaction was performed at 15° C. for 1 hour. After the transformation, the content of rosmarinic acid was measured as 1.5 g/L by liquid chromatography.

Example 10: Synthesis of Rosmarinic Acid by Recombinant *Escherichia coli* Whole-Cell Catalysis The following recombinant strain was constructed: *Escherichia coli* BL21 (DE3)/pRSFDuet-1-ntras-at4cl+pCDFDuet-1-smpkk-ajpkk. According to the method in Example 1, the recombinant strain was induced for expression, and then bacterial cells were collected. In a 100 mL reaction system containing 1 g/L (wet weight) cells, 1 g/L D-Danshensu, 1 g/L caffeic acid, 1 g/L ATP, 1 g/L CoA, and 20 g/L sodium hexametaphosphate, and having a pH of 8, reaction was performed at 40° C. for 48 hours. After the transformation, the content of rosmarinic acid was measured as 1.6 g/L by liquid chromatography. If the concentration of ATP and CoA in the reaction volume is 0 g/L, the content of rosmarinic acid is 0.4 g/L under the condition that other transformation conditions remain unchanged.

Example 11: Synthesis of Rosmarinic Acid by Recombinant *Escherichia coli* Whole-Cell Catalysis The following 2 kinds of recombinant strains were constructed: *Escherichia coli* BL21 (DE3)/pRSFDuet-1-smpkk-ajpkk (named E1), and *Escherichia coli* BL21 (DE3)/pETDuet-1-sc4cl-ccras (named E2).

According to the method in Example 1, E1 and E2 were induced for expression respectively, and then bacterial cells were collected. In a 100 mL reaction system containing 30 g/L (wet weight) E1 cells, 50 g/L (wet weight) E2 cells, 100 g/L D-Danshensu, 10 g/L caffeic acid, 300 g/L sodium hexametaphosphate, 1 g/L CoA, and 0.1 g/L ATP, and having a pH of 9, reaction was performed at 40° C. for 48 hours. After the transformation, the content of rosmarinic acid was measured as 146 g/L by liquid chromatography.

Although the disclosure has been disclosed as above in preferred examples, it is not intended to limit the disclosure. Those skilled in the art can make various changes and modifications without departing from the spirit and scope of the disclosure. Therefore, the protection scope of the disclosure should be defined by the claims.

What is claimed is:

1. A recombinant microbial cell that synthesizes rosmarinic acid from phenolic acids as substrates, comprising:
   a recombinant *Escherichia coli* cell comprising genes that encode and are capable of expressing 4-coumarate: coenzyme A (CoA) ligase, rosmarinic acid synthase, polyphosphate kinase 2-I (PPK2-I), and polyphosphate kinase 2-II (PPK2-II);
   wherein the gene encoding the 4-coumarate: CoA ligase is selected from the group consisting of: sb4cl, ot4cl, ob4cl, pc4cl, sc4cl, and rj4cl;
   wherein the gene encoding the rosmarinic acid synthase is selected from the group consisting of: psras, laras, moras, smras, ccras, ntras, and dcras;
   wherein the gene encoding the PPK2-I is smpkk; and
   wherein the gene encoding the PPK2-II is ajpkk.

2. The recombinant microbial cell according to claim 1, wherein the *E. coli* cell is *E. coli* BL21 (DE3).

3. The recombinant microbial cell according to claim 2, wherein the genes encoding the 4-coumarate: CoA ligase, the rosmarinic acid synthase, the PPK2-I, and the PPK2-II are co-expressed in the recombinant *E. coli* cell from one or more vectors or are integrated into a genome of the recombinant *E. coli* cell.

4. The recombinant microbial cell according to claim 3, wherein the genes encoding the 4-coumarate: CoA ligase, the rosmarinic acid synthase, the PPK2-I, and the PPK2-II are encoded by one or more of four plasmids selected from pETDuet-1, pACYCDuet-1, pRSFDuet-1, and pCDFduet-1, and wherein each of the one or more of four plasmids encodes one or more of the genes encoding the 4-coumarate: CoA ligase, the rosmarinic acid synthase, the PPK2-I, and the PPK2-II.

5. The recombinant microbial cell according to claim 1, wherein the recombinant *E. coli* cell comprises pRSFDuet-1 and pTDuet-1 vectors comprising the genes that encode the PPK2-I, the PPK2-II, and the 4-coumarate: CoA ligase;
   wherein the pRSFDuet-1 vector expresses genes encoding the PPK2-I and the PPK2-II, and the pTDuet-1 vector expresses the gene encoding the 4-coumarate: CoA ligase and the gene encoding the rosmarinic acid synthase; and
   wherein the gene encoding the 4-coumarate: CoA ligase, the gene encoding the rosmarinic acid synthase, the gene encoding the PPK2-I, and the gene encoding the PPK2-II in the recombinant *E. coli* cell each comprise T7 promoters, RBS binding sites, and T7 terminators.

6. A method of producing rosmarinic acid from phenolic acid substrates in a recombinant microbial cell, which comprises:
   providing the recombinant microbial cell according to claim 1,
   culturing the recombinant microbial cell; and
   adding Danshensu and caffeic acid as phenolic substrates to the recombinant microbial cell to produce rosmarinic acid.

7. The method according to claim 6, wherein the culturing step further comprises:
   culturing and propagating the recombinant microbial cell,
   inducing the recombinant microbial cell to express the 4-coumarate: CoA ligase, the rosmarinic acid synthase, the PPK2-I, and the PPK2-II, and
   collecting the recombinant cells.

8. The method according to claim 6, wherein the recombinant cells are incubated at 15° C. to 40° C. for 1 hour to 48 hours in a reaction system comprising:
   1 g/L to 100 g/L of the Danshensu (D or L),
   1 g/L to 100 g/L of the caffeic acid,
   0 g/L to 1 g/L of adenosine triphosphate (ATP),
   0 g/L to 1 g/L of coenzyme A (CoA), and
   300 g/L of sodium hexametaphosphate,
   at a pH value of 5.0 to 9.0.

9. The method according to claim 6, wherein the recombinant cells are incubated at 15° C. to 30° C. for 5 hours to 48 hours in a reaction system comprising D-Danshensu, caffeic acid, coenzyme A (CoA), adenosine triphosphate (ATP), and sodium hexametaphosphate.

10. The method according to claim 6, wherein the recombinant cells are incubated at 40° C. for 48 hours in a reaction system comprising D-Danshensu, caffeic acid, coenzyme A (CoA), adenosine triphosphate (ATP), and sodium hexametaphosphate.

11. Two or more recombinant cells that synthesize rosmarinic acid from phenolic acids as substrates, comprising:
   two or more recombinant cells that are *Escherichia coli* cells that comprise genes that encode and are capable of expressing one or more of 4-coumarate: CoA ligase, rosmarinic acid synthase, polyphosphate kinase 2-II (PPK2-II), and polyphosphate kinase 2-I (PPK2-I);
   wherein each recombinant *E. coli* cell does not repeatedly express one of the 4-coumarate: CoA ligase, the rosmarinic acid synthase, the PPK2-II, and the PPK2-I expressed by the other recombinant *E. coli* cells;
   wherein the gene encoding the 4-coumarate: CoA ligase is selected from the group consisting of: sb4cl, ot4cl, ob4cl, pc4cl, sc4cl, and rj4cl;
   wherein the gene encoding the rosmarinic acid synthase is selected from the group consisting of: psras, laras, moras, smras, ccras, ntras, and dcras;
   wherein the gene encoding the PPK2-I is smpkk; and
   wherein the gene encoding the PPK2-II is ajpkk.

12. The two or more recombinant cells according to claim 11, wherein the *E. coli* is *E. coli* BL21 (DE3).

13. The two or more recombinant cells according to claim 12, wherein the genes encoding the 4-coumarate: CoA ligase, the rosmarinic acid synthase, the PPK2-I, and the PPK2-II are encoded by one or more of four plasmids selected from pETDuet-1, pACYCDuet-1, pRSFDuet-1, and pCDFduet-1, and
  wherein each of the one or more of four plasmids encodes one or more of; the gene encoding the 4-coumarate: CoA ligase, the gene encoding the rosmarinic acid synthase, the gene encoding the PPK2-I, and the gene encoding the PPK2-II.

* * * * *